Jan. 4, 1944. L. C. BOBBINK Plant Pat. 611
AZALEA PLANT
Filed June 21, 1943
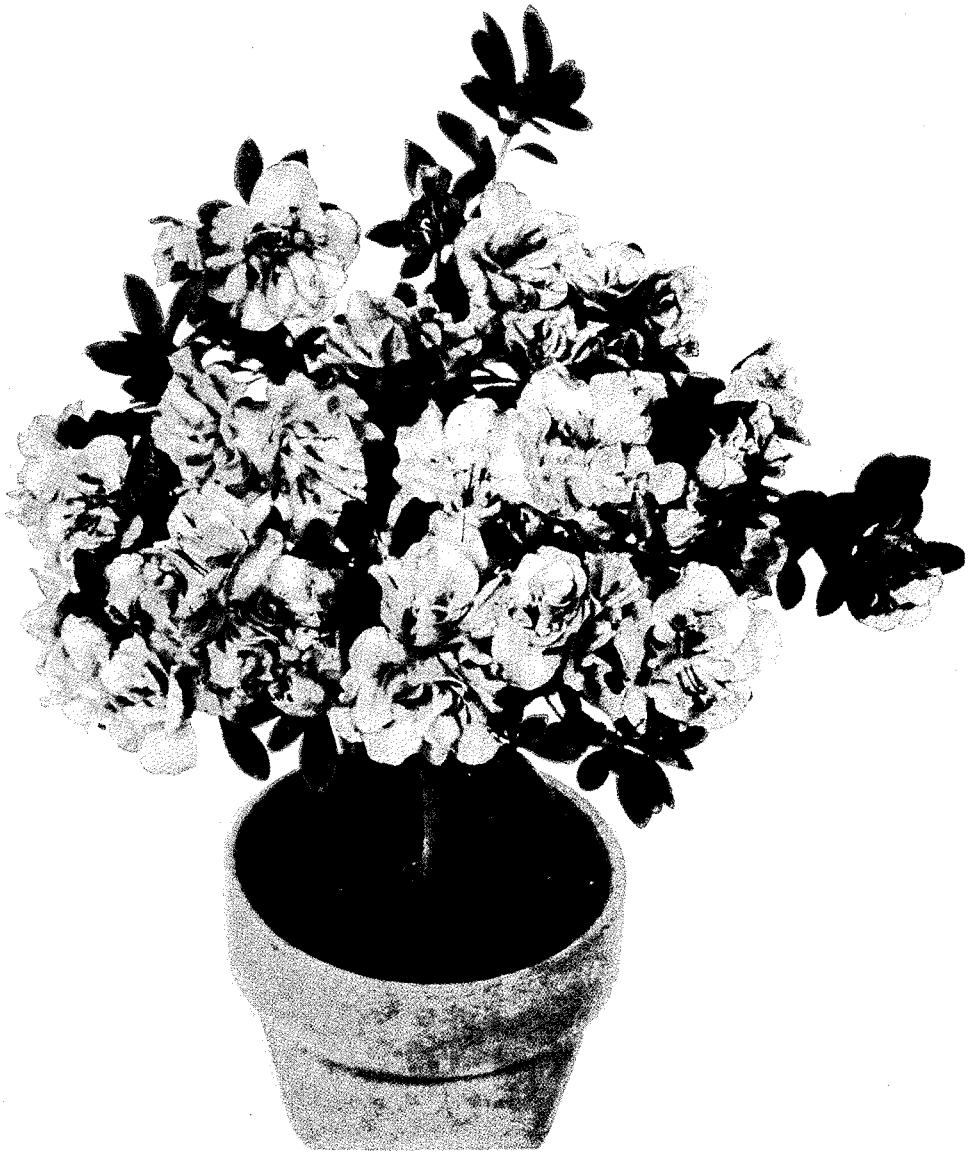
INVENTOR
Lambertus Christian Bobbink
By Orville M. Kile
Plant Patent Agt.

Patented Jan. 4, 1944

Plant Pat. 611

UNITED STATES PATENT OFFICE

611

AZALEA PLANT

Lambertus Christian Bobbink, East Rutherford, N. J., assignor to Bobbink & Atkins, East Rutherford, N. J., a corporation of New Jersey Application June 21, 1943, Serial No. 491,703

1 Claim. (Cl. 47—60)

My present invention relates to a new and distinct variety of azalea plant of the Indica type, and is the result of definite breeding in an effort to produce a superior early flowering forcing azalea.

The results were accomplished by hybridization, and a series of crosses were made over a period of years. At first the Indica variety, Roi Leopold, was crossed with the Indica variety, Apollo. The best seedling was then used as a parent and crossed with the Indica variety, Mrs. Fred Sanders, in an attempt to obtain a larger and earlier flowering variety. In turn, the best early flowering red seedling produced as a result of the best cross was again crossed with the Indica variety, Paul Schame, and the best early flowering seedling resulting from this cross was finally selected as the azalea variety desired.

The new variety is distinct in that it is the nearest-to-true-scarlet azalea known; in that its flowers have better keeping qualities; in that it is a more rapid grower, and is less susceptible to diseases than any existing early-flowering Indica variety now in commerce, such as Mme. Petrick; and in that it grows without aid of grafting. The novel characteristics of this new Indica azalea have been found to be firmly fixed in the asexually reproduced plants.

The accompanying illustration, which is a part of this specification, shows a forced plant of this variety of azalea in approximately its true colors.

The following is a detailed description of the new variety as taken in the greenhouses at East Rutherford, New Jersey. All references to color are in accordance with Koster's Color Guide.

*The plant*

Form: Bush; spreading; branching.

Growth habit: Vigorous; rapid grower. More vigorous than other varieties of Belgian Indica azaleas.

Rooting: Variety is usually grafted on root or understock of azalea coccenea, but cuttings root exceptionally well and can be grown equally well without aid of grafting.

Blooming habit: Profuse. Blooms first year after propagation.

Blooming season: Since this is a forcing variety, the blooming season is dependent upon greenhouse temperature where forced. Under average forcing conditions it can readily be flowered for Christmas.

Foliage: Abundant; individual leaf simple.

*Size.*—Leaf 1½ inches long, ⅜ inch wide (average).

*Color.*—Taxus Green upper side, Reseda Green under side.

*Shape.*—Ovoid, pointed.

*Aspect.*—Evergreen.

*Texture.*—Upper side smooth; under side rough, slightly tomentose.

*Edge.*—Whole.

*Ribs and Veins.*—Ordinary.

*Disease resistance.*—Healthier than average. In greenhouses at East Rutherford it has shown a marked resistance to black spot and other diseases.

*The flower*

Floret:

*Size.*—Large; open floret measures 3½ inches in diameter.

*Borne.*—In clusters of three to five florets.

*Stem.*—Average length ½ inch.

*Form.*—Double—four rows of petals.

*Permanence.*—Excellent endurance and holds color exceptionally well.

*Petalage.*—Averages 21 petals.

*Color.*—Blood-Red.

Petals:

*Texture.*—Thick; leathery.

*Appearance.*—Inside velvety, outside metallic.

*Shape.*—Outside petals pear-shaped and slightly ruffled. Inside petals heart-shaped and very ruffled.

*Arrangement.*—Loose but graceful.

Reproductive organs:

*Stamens.*—Two. Ox-blood Red in color.

*Pollen.*—Crimson-Red.

*Styles.*—Separated; uneven in length; slender.

*Ovaries.*—Normal.

*Comparison*

The variety most nearly like my new variety is the old Belgian Indica azalea, Monsieur Millaud, but the new variety differs from Monsieur Millaud in that it is of much deeper and brighter color. The blooms are larger in size. The plant is more resistant to disease and of more vigorous growth.

Having thus disclosed my invention, I claim: The variety of Indica azalea herein shown and described, characterized particularly by its habit of rapid and vigorous growth; its ability to root unusually well; its early flowering season; its marked freedom from disease; and its large blooms of distinctive blood-red color which last exceptionally well.

LAMBERTUS CHRISTIAN BOBBINK.